United States Patent
Ting et al.

(10) Patent No.: US 9,133,221 B2
(45) Date of Patent: Sep. 15, 2015

(54) METHOD FOR MANUFACTURING HYDROPHILIC SILICONE MACROMER

(71) Applicant: PEGAVISION CORPORATION, Guishan Township, Taoyuan County (TW)

(72) Inventors: Wei-Jia Ting, Guishan Township, Taoyuan County (TW); Heng-Yi Li, Guishan Township, Taoyuan County (TW); Yu-Chin Lai, Guishan Township, Taoyuan County (TW); Han-Yi Chang, Guishan Township, Taoyuan County (TW)

(73) Assignee: PEGAVISION CORPORATION (TW)

( * ) Notice: Subject to any disclaimer, the term of this patent is extended or adjusted under 35 U.S.C. 154(b) by 0 days.

(21) Appl. No.: 14/469,386

(22) Filed: Aug. 26, 2014

(65) Prior Publication Data

US 2014/0364624 A1    Dec. 11, 2014

Related U.S. Application Data

(62) Division of application No. 13/715,658, filed on Dec. 14, 2012, now Pat. No. 8,865,925.

(30) Foreign Application Priority Data

Dec. 29, 2011 (TW) ............................. 100149573 A

(51) Int. Cl.
| | | |
|---|---|---|
| *C07F 7/08* | (2006.01) | |
| *C07F 7/10* | (2006.01) | |
| *C07F 9/06* | (2006.01) | |
| *C08G 77/388* | (2006.01) | |
| *G02B 1/04* | (2006.01) | |

(52) U.S. Cl.
CPC . *C07F 7/10* (2013.01); *C07F 9/062* (2013.01); *C08G 77/388* (2013.01); *G02B 1/043* (2013.01)

(58) Field of Classification Search
CPC ...................................................... C07F 7/0838
USPC ............................................................ 556/450
See application file for complete search history.

(56) References Cited

U.S. PATENT DOCUMENTS

| | | | |
|---|---|---|---|
| 4,136,250 A | 1/1979 | Mueller et al. | 528/29 |
| 4,259,467 A | 3/1981 | Keogh et al. | 526/279 |
| 4,260,725 A | 4/1981 | Keogh | 526/279 |
| 5,516,869 A | 5/1996 | Lucarelli et al. | 528/15 |
| 6,087,412 A | 7/2000 | Chabrecek et al. | 522/35 |
| 6,573,328 B2 | 6/2003 | Kropp et al. | 524/588 |
| 7,423,074 B2 * | 9/2008 | Lai et al. | 523/106 |
| 7,452,377 B2 | 11/2008 | Watling et al. | 623/6.11 |
| 8,129,442 B2 | 3/2012 | Ueyama et al. | 523/107 |
| 8,163,206 B2 | 4/2012 | Chang et al. | 264/1.38 |
| 8,207,245 B2 | 6/2012 | Padsalgikar et al. | 523/113 |
| 8,524,849 B2 | 9/2013 | Stark | 528/32 |
| 2004/0054026 A1 | 3/2004 | Kunzler et al. | 523/106 |
| 2007/0142583 A1 | 6/2007 | Schorzman et al. | 526/264 |
| 2009/0163602 A1 | 6/2009 | Hu et al. | 514/772.4 |
| 2010/0258961 A1 | 10/2010 | Chang et al. | 264/1.38 |

FOREIGN PATENT DOCUMENTS

| | | | |
|---|---|---|---|
| CN | 1171798 | 1/1998 | C08F 283/12 |
| CN | 1681862 | 10/2005 | A61F 2/14 |
| CN | 101039982 | 9/2007 | A61L 27/16 |
| CN | 101263182 | 9/2008 | C08F 2/00 |
| CN | 101469068 | 7/2009 | C08G 77/46 |
| CN | 102257408 | 11/2011 | G02B 1/04 |
| JP | 56-94324 | 7/1981 | G02C 7/04 |
| JP | 2000-319398 | 11/2000 | C08G 77/388 |
| JP | 2003-192790 | 7/2003 | C08G 77/20 |
| WO | WO 2009/099164 | 8/2009 | C08G 77/38 |
| WO | WO 2010/14779 | 12/2010 | C08G 77/395 |
| WO | WO 2011/116210 | 9/2011 | G02C 7/04 |

* cited by examiner

*Primary Examiner* — Shawquia Jackson
(74) *Attorney, Agent, or Firm* — Hayes Soloway P.C.

(57) ABSTRACT

A method for manufacturing a hydrophilic silicone macromer is provided. A hydrosilylation between a Si—H bond of a polysiloxane and a C=C bond of a hydrophilic mononmer is performed by using a rhodium-containing catalyst to form the polysiloxane having a hydrophilic side chain having an amide group or a phosphoryl choline group. After performing an end-capping reaction, the hydrophilic silicone macromer is formed.

9 Claims, No Drawings

METHOD FOR MANUFACTURING HYDROPHILIC SILICONE MACROMER

RELATED APPLICATIONS

The present application is a Divisional Application of the application Ser. No. 13/715,658, filed Dec. 14, 2012, the entire contents of which are hereby incorporated herein by reference, which claims priority to Taiwan Application Serial Number 100149573, filed Dec. 29, 2011, all of which are herein incorporated by reference.

BACKGROUND

1. Technical Field

The present disclosure relates to a contact lens material, and more particularly, to a method for manufacturing a hydrophilic silicone macromer used in a contact lens.

2. Description of Related Art

Silicone hydrogel has long been considered as one of contact lens materials because of its high oxygen permeability. Silicone hydrogel lens can deliver a sufficient amount of oxygen to a cornea, and thus is suitable for long-time wearing and less likely to cause eye complications.

The composition of a silicone hydrogel contact lens typically contains one or more kinds of silicone-based monomers, macromers and prepolymers. A silicone monomer usually has at most 4 silicon atoms, and its molecular weight typically is less than 500 daltons, such as 3-(methacryloyoxypropy)-trs(trimethylsiloxy)silane (TRIS). A silicone macromer has linear siloxane units and an ethylenically unsaturated polymerizable group, and its molecular weight usually is higher than 500 daltons. A silicone prepolymer has linear siloxane units and two ethylenically unsaturated polymerizable groups. Silicones are highly hydrophobic material, and how to enhance the wettability of a silicone hydrogel lens becomes a challenge.

There are some methods for improving the wettability of a silicone hydrogel lens, such as performing a plasma process on the surface of the silicone-containing hydrophobic lens, adding hydrophilic polymers such as polyvinylpyrrolidone to a silicone hydrogel composition, or using a silicone-based prepolymer having polyethylene oxide side chains. Keogh et al. (the U.S. Pat. No. 4,259,467) disclosed structures of hydrophilic silicone-based monomers, macromers and pre-polymers; however, no effective method for manufacturing a hydrophilic silicone macromer has ever been disclosed especially for those containing amide or phosphoryl choline hydrophilic side chains.

Therefore, there is a need for an effective method for manufacturing hydrophilic silicone macromer and the macromer made therefrom to solve the problems in the art.

SUMMARY

One aspect of the present disclosure provides a method for manufacturing hydrophilic silicone macromer, which includes the steps below. A ring-opening insertion is performed, in which a cyclic siloxane and a cyclic hydrogen siloxane are subjected to a ring-opening reaction, and then are inserted into a linear polysiloxane having a terminal reactive hydrogen to form a reactive hydrogen-terminated polysiloxane having a silicon-hydrogen (Si—H) bond. The terminal reactive hydrogen is derived from a hydroxyl group or an amino group. A hydrosilylation between the Si—H bond of the reactive hydrogen-terminated polysiloxane and a C=C bond of a hydrophilic monomer is performed by using a rhodium-containing catalyst to form a reactive hydrogen-terminated polysiloxane intermediate having a hydrophilic side chain. The hydrophilic monomer has an amide group or a phosphoryl choline group. An end-capping reaction between the terminal reactive hydrogen of the polysiloxane intermediate and an electrophilic group of an ethylenically unsaturated compound is performed to form the hydrophilic silicone macromer.

The manufacturing method mentioned above can be employed to effectively synthesize hydrophilic silicone macromer used in making silicone hydrogel lenses.

DETAILED DESCRIPTION

The present disclosure is described by the following specific embodiments. Those with ordinary skill in the arts can readily understand other advantages and functions of the present invention after reading the disclosure of this specification. The present disclosure can also be implemented with different embodiments. Various details described in this specification can be modified based on different viewpoints and applications without departing from the scope of the present disclosure.

As used herein, the singular forms "a," "an" and "the" include plural referents unless the context clearly dictates otherwise. Therefore, reference to, for example, a data sequence includes aspects having two or more such sequences, unless the context clearly indicates otherwise.

Reference will now be made in detail to the embodiments of the present disclosure, examples of which are illustrated in the accompanying drawings. Wherever possible, the same reference numbers are used in the drawings and the description to refer to the same or like parts.

One aspect of the present disclosure provides a method for manufacturing a hydrophilic silicone macromer, which includes a ring-opening insertion, a hydrosilylation and an end-capping reaction. The reaction schemes are shown in Chemical Schemes (1), (2) and (3).

First, the ring-opening insertion is performed, as shown in Chemical Scheme (1).

Chemical Scheme (1)

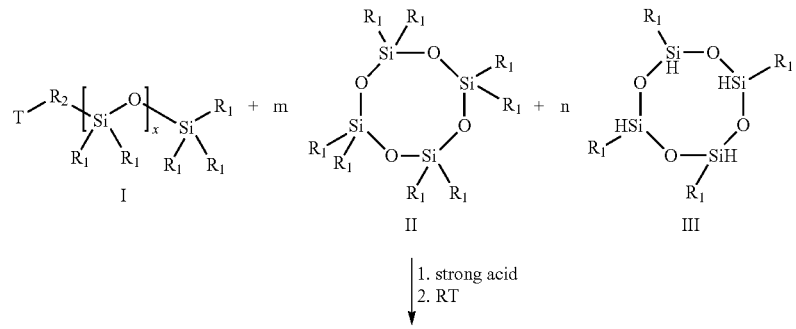

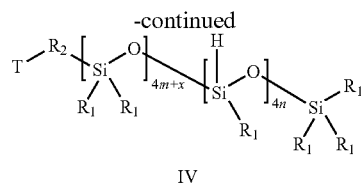

IV

At least one cyclic siloxane II and at least one cyclic hydrogen siloxane III perform the ring-opening reaction, and then inserted into a linear polysiloxane I to form a polysiloxane IV having a silicon-hydrogen (Si—H) bond. The reaction can be performed in an ambient temperature. The rings of the cyclic siloxane II and the cyclic hydrogen siloxane III are opened by a strong acid, and thus forming linear siloxane repeating units. The strong acid may be triflic acid or sulfuric acid. Next, the linear siloxane repeating units are inserted to the linear polysiloxane I, and then forming the polysiloxane IV having an even higher molecular weight. In Chemical Scheme (1), the cyclic hydrogen siloxane III is ring-opened and then inserts into the linear polysiloxane I to introduce a silicon-hydrogen (Si—H) bonds therein. The Si-H bond can react with a compound having a C=C bond (i.e., hydrosilylation). In addition, the cyclic siloxane II and the cyclic hydrogen siloxane III can be used to increase the molecular weight of the polysiloxane IV.

The linear polysiloxane I has a general formula T-$R_2$—[Si($R_1$)$_2$O]—Si($R_1$)$_3$. T is an amino group or a hydroxyl group, and has at least one terminal reactive hydrogen. $R_2$ is —$(CH_2)_b$—O—$(CH_2)_c$— or a C3-C6 alkyl group. b is 2 to 4, and c is 2 to 4. The linear polysiloxane I may be butyl [(hydroxyethoxy)propyl] polydimethylsiloxane.

The amounts of the siloxane repeating units of the cyclic siloxane II and the cyclic hydrogen siloxane III may respectively be 3 to 5. For instance, the cyclic siloxane II and the cyclic hydrogen siloxane III respectively are 1,1,3,3,5,5,7,7-octamethylcyclotetrasiloxane and 1,3,5,7-tetramethyltetrasiloxane.

The formed polysiloxane IV has Si—H bonds and the terminal group T having a reactive hydrogen. The terminal reactive hydrogen is derived from a hydroxyl group or an amino group and used to react with an electrophilic group. The another group Si($R_1$)$_3$ of the polysiloxane IV may be a non-reactive alkyl group. The siloxane repeating units of the polysiloxane IV include —[($R_1$)$_2$SiO]— and —[($R_1$)(H)SiO]—. The amounts of the —[($R_1$)$_2$SiO]— and —[($R_1$)(H)SiO]— respectively are (4m+x) and 4n. Two kinds of siloxane repeating units mentioned above can be randomly arranged.

Subsequently, the hydrosilylation is performed, as shown in Chemical Scheme (2).

Chemical Scheme (2)

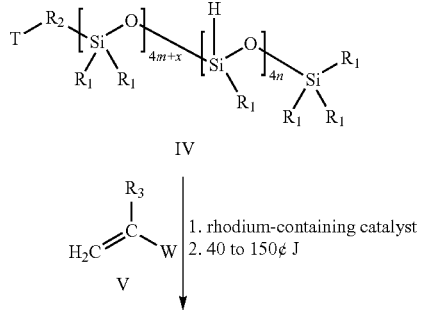

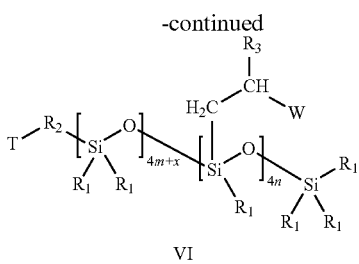

VI

The hydrosilylation between the Si—H bond of the polysiloxane IV and a C=C bond of a hydrophilic monomer V is performed to form a reactive hydrogen-terminated polysiloxane intermediate VI having a hydrophilic side chain. The hydrophilic monomer V has an amide group or a phosphoryl choline group. The reaction can be performed in an environment of 40 to 150° C. The wettability of the polysiloxane intermediate VI can be increased by inserting the hydrophilic side chain thereinto (i.e., hydrosilylation).

The catalyst used in the hydrosilylation can be a rhodium-containing complex, such as tris(dibutylsulfide)rhodium trichloride. Generally, the metal complex containing rhodium or platinum can be acted as the catalyst for hydrosilylation. However, the inventors found that the rhodium-containing catalyst has much better catalytic effect of the hydrosilylation, and the platinum-containing catalyst has poor catalytic effect thereof for the hydrosilation involving hydrophilic monomer containing amide or phosphoryl choline groups from experimental results. Accordingly, the inventors speculated that platinum loses catalytic activity because the hydrophilic monomer has a nitrogen atom or a phosphorus atom.

The hydrophilic monomer V has a general formula $CH_2$=C($R_3$)W. $R_3$ is a hydrogen or a methyl group. W has an amide group or a phosphoryl choline group, such as the structures of chemical formulas (1), (2) or (3).

Chemical formula (1)

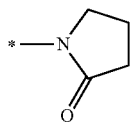

Chemical formula (2)

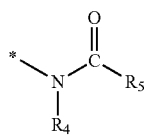

In Chemical formula (2), $R_4$ is a C1-C4 alkyl group, and $R_5$ is a C1-C4 alkyl group.

Chemical formula (3)

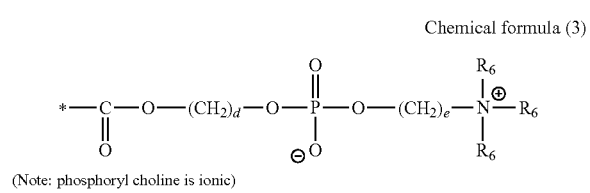

(Note: phosphoryl choline is ionic)

In Chemical formula (3), $R_6$ is a C1-C3 alkyl group. d is 2 to 4, and e is 2 to 4.

The hydrophilic monomer V having an amide group can be N-vinylpyrrolidone, N-allylpyrrolidone (refers to Chemical formula (1)) or N-vinyl-N-methylacetamide (refers to Chemical formula (2)). The hydrophilic monomer V having the phosphoryl choline group can be 2-methacryloyloxyethyl phosphorylcholine (MPC) (refers to Chemical formula (3)).

Next, the end-capping reaction is performed, as shown in Chemical Scheme (3).

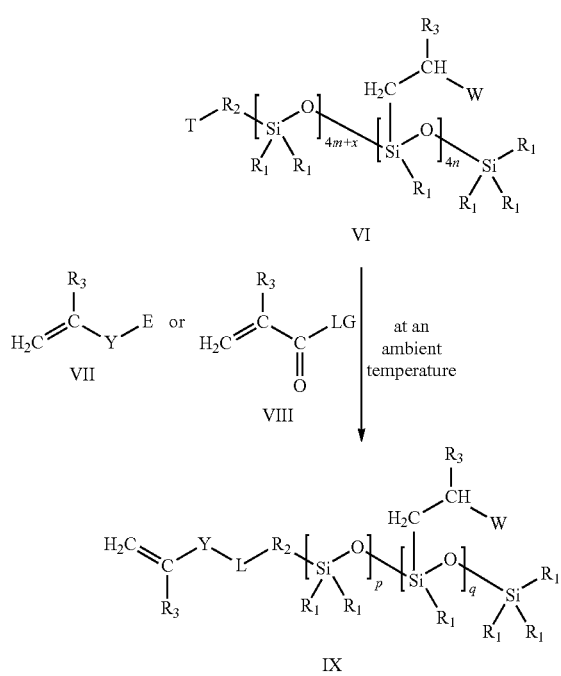

The terminal reactive hydrogen of the polysiloxane intermediate VI is reacted with the electrophilic group of an ethylenically unsaturated compound VII or VIII to form the hydrophilic silicone macromer IX.

Various bonds can be formed by the reactions between the reactive hydrogen of the polysiloxane intermediate VI derived from an amino group or a hydroxyl group and various electrophilic groups. The amino group, which is the terminal group T of the polysiloxane intermediate VI, can react with an isocyanate group to form a urea linkage. The amino group also can react with an anhydride or an acyl chloride to form an amide linkage. The hydroxyl group, which is the terminal group T of the polysiloxane intermediate VI, can react with an isocyanate group to form a carbamate linkage. The hydroxyl group also can react with an anhydride or an acyl chloride group to form an ester linkage.

The ethylenically unsaturated compound has a general formula $CH_2=C(R_3)$—Y-E (VII) or $CH_2=C(R_3)$—CO-LG (VIII).

When the general formula is $CH_2=C(R_3)$—Y-E (VII), $R_3$ is a hydrogen or a methyl group. E is an electrophilic group, such as an isocyanate group. Y is —$(CH_2)_f$— or —COO $(CH_2)_g$—. f is 0 to 4, and g is 2 to 4. The ethylenically unsaturated compound can react with an amino group or a hydroxyl group, and $CH_2=C(R_3)$—Y-L- is formed. L is a linkage group, such as —NHCOO— or —NHCONH—. The ethylenically unsaturated compound VII may be isocyanatoethyl methacrylate.

When the general formula is $CH_2=C(R_3)$—CO-LG (VIII), LG is a chloride atom or an anhydride group. The ethylenically unsaturated compound can react with an amino group or a hydroxyl group, and $CH_2=C(R_3)$—Y-L- is formed. Y is —$(CH_2)_f$—, and f is 0. That is, the general formula $CH_2=C(R_3)$—Y-L- is $CH_2=C(R_3)$-L-, and L is —COO— or —CONH—. The ethylenically unsaturated compound VIII may be methacryloyl chloride or methacrylic anhydride.

In one embodiment, the hydrophilic monomer V used in the hydrosilylation is in a range of about 5 to about 90wt %, based on the total weight of the hydrophilic silicone macromer IX to be manufactured. For an example, the hydrophilic monomer V is in a range of about 22 to about 35wt %, based on the total weight of the hydrophilic silicone macromer IX.

The amounts of —$[(R_1)_2SiO]$— and the —$[(R_1)(H)SiO]$— of the synthesized hydrophilic silicone macromer IX respectively are p and q. The hydrophilic macromer IX has a number average molecular weight (Mn) in a range of about 500 to about 6000.

The hydrophilic silicone macromer can be used in the biomedical field, particular as the main component of a silicone hydrogel lens, but not limited thereto. For an example, the mixture composed of a silicone macromer and other components is placed in a plastic mold, and then cured by UV light or thermal energy. The next steps such as hydration and sterilization are performed, and a silicone hydrogel lens is obtained.

Embodiments

The following examples are provided to illustrate certain aspects of the present disclosure and to aid those of skill in the art in practicing this disclosure. These examples are in no way to be considered to limit the scope of the disclosure in any manner.

EXAMPLE 1

Preparation of Macromer 1 Having Side Chain with Pyrrolidone Group

Ring-Opening Insertion 29.6 g (0.1mole) 1,3,3,5,5,7,7-octamethylcyclotetrasiloxane, 24.0 g (0.1 mole) 1,3,5,7-tetramethyl-cyclotetrasiloxane, 93.5 g (0.1 mole) butyl [(hydroxyethoxy)propyl] polydimethylsiloxane and 1.2 mg trifluoromethanesulfonic acid were putted into a 1-L-3-necked round bottom flask equipped with a reflux condenser and a nitrogen blanket. The molar ratio of 1,3,3,5,5,7,7-octamethylcyclotetrasiloxane, 1,3,5,7-tetramethyl-cyclotetrasiloxane and butyl [(hydroxyethoxy) propyl] polydimethylsiloxane is 1:1:1. The mixture was stirred for 24 hours at 25° C., and a solution is then formed.

Next, reactive hydrogen terminated-polysiloxane having Si—H bonds was obtained after extracting the solution for several times. For instance, a first extraction step was performed. 200 ml ether and 350 ml water were added into the solution, and the aqueous layer was then removed. The organic layer was washed twice with water and converted to neutral. Ether of the organic layer was stripped, and a crude product was formed.

A second extraction step was performed. 225 ml methanol and 75 ml water were added into the aforementioned crude product and stirred for 30 minutes, and the aqueous layer was then removed. The organic layer was diluted with 60 ml ether, and then dried by 40 g magnesium sulfate. Subsequently, ether was stripped under reduced pressure, and transparent viscous liquid (productivity: 81%) is obtained, which is the reactive hydrogen terminated-polysiloxane having Si—H bonds. The polymer of the viscous liquid was a random copolymer.

Proton NMR data of butyl [(hydroxyethoxy)propyl] polydimethylsiloxane: 0.0 ppm (Si—$CH_3$, 78H), 0.50 ppm (Si—$CH_2$—, 4H), 0.86 ppm (terminal $CH_3$, 3H), 1.30 ppm (Si—$CH_2CH_2$—, 4H), 1.60 ppm ($CH_2$, 2H), 2.29 ppm (OH, 1H), 3.45 ppm (O—$CH_2$, 2H), 3.56 ppm (HO—$CH_2$—, 2H) and 3.73 ppm (O—$CH_2$, 2H). The result indicated that this compound has 12.8 dimethylsiloxane repeating units in average.

Proton NMR data of the viscous liquid: 0.0 ppm (Si—$CH_3$, 123H), 0.50 ppm (Si—$CH_2$—4H), 0.86 ppm (terminal $CH_3$, 3H), 1.30 ppm (Si—$CH_2CH_2$—, 4H), 1.60 ppm ($CH_2$, 2H), 2.0 ppm (OH, 1H), 3.45 ppm (O—$CH_2$, 2H), 3.56 ppm (HO—$CH_2$—, 2H), 3.73 ppm (O—$CH_2$, 2H) and 4.67 ppm (Si—H, 4.1). The result indicated that this compound has 17.5 dimethylsiloxane repeating units and 4.1 hydromethylsiloxane repeating units in average. That is, the hydromethylsiloxane repeating units was 19% based on the total number of the siloxane repeating units.

Hydrosilylation 35 g (0.315 mol) N-vinylpyrrolidone and 50 ml toluene were putted into a 250-ml-3-necked round bottom flask equipped with a reflux condenser and a nitrogen blanket, and then stirred and heated to 110° C. Next, the solution was cooled to 100° C. 0.3 g tris(dibutylsulfide)rhodium trichloride and 116.15 g of the aforementioned viscous liquid were added into the round bottom flask, and continuously heated and stirred for 1 hour. Toluene was removed under reduced pressure until the Si—H band (2127 $cm^{-1}$) of the mixture measured by IR spectrometer has disappeared. Next, the mixture was cooled to an ambient temperature, and the hydrophilic polysiloxane intermediate having the hydrophilic side chains is obtained.

End-Capping Reaction 140.0 g (0.073 mole) hydrophilic polysiloxane intermediate, 16 g (0.106 mole) isocyanatoethyl methacrylate, 50 ml dry dichloromethane, 16.5 mg methylhydroquinone and 0.495 mg dibutyltin dilaurate (DBTDL) were putted into a 250-ml-3-necked round bottom flask equipped with a reflux condenser and a nitrogen blanket, and stirred for 60 hours at an ambient temperature. 5 ml methanol was then added and stirred for 2 hours. Dichloromethane was stripped under reduced pressure, and a crude product is obtained. Next, an extraction step was performed. 120 ml methanol and 70 ml water were added into the crude product and stirred for 30 minutes, and the aqueous layer was then removed. The organic layer was washed twice with water, diluted with 200 ml dichloromethane, dried by 50 g magnesium sulfate and filtered in sequence. 16.5 mg methylhydroquinone was added into the organic layer after filtering. Finally, dichloromethane was removed, and 131 g viscous hydrophilic silicone macromer is obtained.

Proton NMR data of the hydrophilic silicone macromer: 0.0 ppm (Si—$CH_3$, 112H), 0.53 ppm (Si—$CH_2$—, 4H), 0.88 ppm (terminal $CH_3$, 3H), 1.15 ppm (H of pyrrolidone), 1.30 ppm (Si—$CH_2CH_2$—, 4H), 1.60 ppm ($CH_2$, 2H), 1.94 ppm (C=C—$CH_3$, 3H), 1.94-2.34 ppm (H of OH of pyrrolidone, 1H), 33-3.8 ppm (O—$CH_2$—$CH_2$—O—, H of pyrrolidone), 5.58 ppm (C=C—H, 1H) and 6.13 ppm (C=C—H, 1H).

EXAMPLE 2

Preparation of Contact Lens

The hydrophilic silicone macromer, N-vinylpyrrolidone, 2-hydroxyethyl methacrylate, isobornyl methacrylate, ethylene glycol dimethacrylate, triallylisocyanurate, t-amyl alcohol and azo bis isobutyl nitrile were mixed in a weight ratio of 65:30:5:5:0.2:0.3:10:1. Next, the mixture was filtered by a 0.5 μm filter and then filled into a polypropylene mold. Next, the hydrophilic polymer was cured under the condition of 55° C./1.5 hr, 70° C./0.5 hr, 90° C./0.5 hr, 110° C./0.5 hr in sequence and then cooled to an ambient temperature. The lenses were released and extracted with isopropanol for 4 hours. The lenses were dipped into 50/50 isopropanol/water for 30 minutes, and then dipped into distilled water for 30 minutes. Next, the lenses were placed into a glass vial filled with borate-containing physiological saline buffer solution and autoclaved at 121° C. for 30 minutes. The water content of the lenses was 58.1%.

EXAMPLE 3

Preparation of Macromer 2 Having Side Chain with Pyrrolidone Group

The experimental steps of Example 3 are the same as those of Example 1. The differences are that the ratio of the used components and the weights of the products of each step. The weight or the volume of each component and that of each product are described below.

Ring-Opening Insertion

The components are 88 g butyl [(hydroxyethoxy)propyl] polydimethylsiloxane, 47.36 g 1,3,3,5,5,7,7-octamethylcyclotetrasiloxane, 47.36 g 1,3,5,7-tetramethyl-cyclotetrasiloxane and 3.35 mg trifluoromethanesulfonic acid. The formed viscous liquid is 204.5 g (productivity: 95%). The molar ratio of 1,3,3,5,5,7,7-octamethylcyclotetrasiloxane, 1,3,5,7-tetramethyl-cyclotetrasiloxane and butyl [(hydroxyethoxy)propyl]polydimethylsiloxane is 1:1:2.

Hydrosilylation

The components are 76.28 g N-vinylpyrrolidone, 109.6 ml toluene, 0.2193 g tris(dibutylsulfide)rhodium trichloride and 143 g aforementioned viscous liquid. The formed hydrophilic polysiloxane intermediate is 212 g.

End-Capping Reaction

The components are 213 g hydrophilic polysiloxane intermediate, 10.65 g isocyanatoethyl methacrylate, 0.0223 g methylhydroquinone, 0.3345 mg dibutyltin dilaurate (DBTDL) and 100 ml dry dichloromethane. The formed hydrophilic macromer is 120 g.

EXAMPLE 4

Preparation of Macromer Having Side Chain with Phosphoryl Choline Group

The experimental steps of Example 4 are the same as those of Example 1. The difference is that 0.315 mole 2-methacryloyloxyethyl phosphorylcholine is used as the hydrophilic monomer of hydrosilylation. Finally, the macromer having a side chain with a phosphoryl choline group is obtained.

Although the present disclosure has been described in considerable details with reference to certain embodiments thereof, other embodiments are possible. Therefore, the spirit and scope of the appended claims should not be limited to the description of the embodiments contained herein.

It will be apparent to those ordinarily skilled in the art that various modifications and variations may be made to the structure of the present disclosure without departing from the scope or spirit of the disclosure. In view of the foregoing, it is intended that the present disclosure cover modifications and variations thereof provided they fall within the scope of the following claims.

What is claimed is:

1. A method for manufacturing a hydrophilic silicone macromer, comprising the steps of:

performing a ring-opening insertion, wherein a cyclic siloxane and a cyclic hydrogen siloxane are subject to a ring-opening reaction, and then are inserted into an asymmetrically end-capped polydialkylsiloxane having a terminal reactive hydrogen to form an asymmetrically end-capped polysiloxane having a silicon-hydrogen (Si-H) bond, in which the terminal reactive hydrogen is derived from a hydroxyl group or an amino group;

performing a hydrosilylation between the Si-H bond of the asymmetrically end-capped polysiloxane and a C=C bond of a hydrophilic monomer by using a rhodium-containing catalyst to form an asymmetrically end-capped polysiloxane intermediate having a hydrophilic side chain, wherein the hydrophilic monomer has an amide group or a phosphoryl choline group; and performing an end-capping reaction between the terminal reactive hydrogen of the asymmetrically end-capped polysiloxane intermediate and an electrophilic group of an ethylenically unsaturated compound to form the hydrophilic silicone macromer having only one ethylenically unsaturated group.

2. The method of claim 1, wherein the step of performing the hydrosilylation is in an environment of 40 to 150° C.

3. The method of claim 1, wherein the hydrophilic monomer having the amide group selected from the group comprising N-vinylpyrrolidone, N-allylpyrrolidone, N-vinyl-N-methylacetamide and a combination thereof.

4. The method of claim 1, wherein the hydrophilic monomer having a phosphoryl choline group is 2-methacryloyloxyethyl phosphorylcholine.

5. The method of claim 1, wherein the rhodium-containing catalyst is tris(dibutylsul fide)rhodium trichloride.

6. The method of claim 1, wherein the hydrophilic silicone macromer has a molecular weight in a range of about 500 to about 6,000.

7. The method of claim 1, wherein the weight ratio of the hydrophilic monomer used for the hydrosilylation and the hydrophilic silicone macromer to be manufactured is in a range of about 5:100 to about 90:100.

8. The method of claim 1, wherein the cyclic siloxane is 1,1,3,3,5,5,7,7-octamethylcyclotetrasiloxane, and the cyclic hydrogen siloxane is 1,3,5,7-tetramethyltetrasiloxane.

9. The method of claim 1, wherein the ethylenically unsaturated compound is selected from the group comprising isocyanatoethyl methacrylate, methacryloyl chloride, methacrylic anhydride and a combination thereof.

* * * * *